United States Patent [19]

Knutsen et al.

[11] Patent Number: 5,229,404
[45] Date of Patent: Jul. 20, 1993

[54] AZACYCLIC CARBOXYLIC ACID DERIVATIVES AND THEIR PREPARATION AND USE

[75] Inventors: Lars J. S. Knutsen, Vedbaek; Knud E. Andersen, Bagsvaerd; Anker S. Jorgensen, Copenhagen; Ursula Sonnewald, Ballerup, all of Denmark

[73] Assignee: Novo Nordisk A/S, Bagvaerd Denmark, Denmark

[21] Appl. No.: 804,903

[22] Filed: Dec. 6, 1991

Related U.S. Application Data

[62] Division of Ser. No. 554,246, Jul. 17, 1990, which is a division of Ser. No. 350,151, May 10, 1989, Pat. No. 5,039,685.

[30] Foreign Application Priority Data

May 18, 1988 [DK] Denmark .................... 2704/88

[51] Int. Cl.⁵ .................. C07D 213/53; C07D 233/66; C07D 207/30; A61K 31/44
[52] U.S. Cl. .................... 514/357; 514/399; 514/400; 514/427; 514/524; 514/640; 546/333; 548/561; 548/332.5; 548/326.5; 558/418; 564/256
[58] Field of Search ............... 548/341, 343, 561, 566; 546/333; 558/418; 564/256; 514/357, 359, 400, 427, 524, 640

[56] References Cited

U.S. PATENT DOCUMENTS

| | | | |
|---|---|---|---|
| 4,358,450 | 11/1982 | Gebert | 546/201 |
| 4,722,930 | 2/1988 | Archibald et al. | 546/214 |
| 4,772,615 | 9/1988 | Pavia | 514/318 |
| 5,006,560 | 4/1991 | Kreutner | 514/567 |
| 5,043,327 | 8/1991 | Freyne | 544/230 |

OTHER PUBLICATIONS

Rossi et al. "p-Dialchilaminoetilchetossimne . . ." Farma Ed. Sci XIX 688-702 (1964).

*Primary Examiner*—C. Warren Ivy
*Assistant Examiner*—Celia Chang
*Attorney, Agent, or Firm*—Gordon W. Hueschen

[57] ABSTRACT

Novel O-alkylated oximes of the general formula I

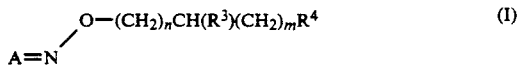

wherein

A is 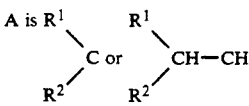

wherein $R^1$ and $R^2$ are optionally substituted aromatic or heteroaromatic rings, $R^3$ is hydrogen or lower alkyl, $R^4$ is a nitrogen containing, substituted ring or an amino group carrying a substituted ring, and n and m independently are 0, 1 or 2, are potent inhibitors of GABA re-uptake from the synaptic cleft.

20 Claims, No Drawings

AZACYCLIC CARBOXYLIC ACID DERIVATIVES AND THEIR PREPARATION AND USE

The present application is a division of our prior-filed copending U.S. application Ser. No. 07/554,246, filed Jul. 17, 1990, which in turn is a division of our prior-filed copending U.S. application Ser. No. 07/350,151, filed May 10, 1989, now U.S. Pat. No. 5,039,685, issued Aug. 13, 1991.

The present invention relates to novel O-alkylated oximes and salts thereof, to methods for their preparation, to compositions containing them, and to their use for the clinical treatment of abnormal functioning of the γ-aminobutyric acid neurotransmission system.

In recent years much pharmacological research concerning γ-aminobutyric acid (hereinafter designated GABA), which is an inhibitory neurotransmitter in the mammalian central nervous system, has been carried out.

The inhibition of GABA re-uptake results in the enhancement of availability of this inhibitory neurotransmitter in the synaptic cleft leading to increased GABA'-ergic activity. Increased GABA'ergic activity can be useful in the treatment, for example, of anxiety, pain and epilepsy as well as muscular and movement disorders (see for example, *Progress in Medicinal Chemistry* 22 (1985) 68-112 (edited by G. P. Ellis and G. B. West, Elsevier Science Publishers, B.V.).

As well-known and potent inhibitor of GABA re-uptake from the synaptic cleft into presynaptic nerve terminals and glial cells is, for example, piperidine-3-carboxylic acid (nipecotic acid). However, being a relatively polar compound and therefore unable to cross the blood-brain b arrier, piperidine-3-carboxylic acid itself has found no practical utility as a drug. In U.S. Pat. Nos. 4,383,999 and 4,514,414 (SmithKline Beckman Corporation) and European patent applications no. 86903274 and no. 87300064 (Novo Industri A/S) some derivatives of N-(4,4-disubstituted-3-buten-1-yl)azaheterocyclic carboxylic acids are claimed as inhibitors of GABA uptake. Furthermore, European patent application no. 86115478.9 (Warner-Lambert Company) claims that 1-aryloxyalkylpyridine-3-carboxylic acids are also inhibitors of GABA re-uptake.

According to *J.Pharm.Exp.Therap.* 228 (1984) 109, N-(4,4-diphenyl-3-buten-1-yl)nipecotic acid (designated SK&F 89976A), N-(4,4-diphenyl-3-buten-1-yl)guvacine (designated SK&F 100330A), N-(4,4-diphenyl-3-buten-1-yl)homoβ-proline (designated SK&F 100561) and N-(4-phenyl-4-(2-thienyl)-3-buten-1-yl)nipecotic acid (designated SK&F 100604J) are oral inhibitors of GABA uptake. These data are summarized in *Epilepsy Res.* 1 (1987) 77-93.

Guvacine is 1,2,5,6-tetrahydro-pyridine-3-carboxylic acid and homo-β-proline is pyrrolidine-3-acetic acid.

The present invention relates to novel O-substituted oximes in which the O-substituent contains either a derivative of piperidine-3-carboxylic acid (nipecotic acid) or of another GABA-mimetic, cyclic amino acid moiety of the general formula II, III or IV. The compounds according to the invention have the general formula I $$A = NO\text{-}(CH_2)_n CH(R^3)(CH_2)_m R^4 \quad (I)$$

wherein

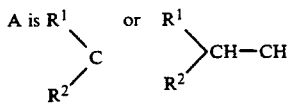

wherein $R^1$ and $R^2$ are the same or different and each represent furanyl, imidazolyl, oxazolyl, phenyl, pyrazolyl, pyrazinyl, pyridazinyl, pyridyl, pyrimidinyl, pyrrolyl, thiazolyl, thienyl or 1,2,4-triazolyl. Each of these may be optionally substituted by one, two or three substituents selected from the group consisting of lower alkylamino, lower alkylthio, lower alkoxy, amino, azido, cyano, halogen, hydroxy, lower alkyl, nitro, mercapto and trifluoromethyl. $R^3$ represents hydrogen or lower alkyl and n and m are independently 0, 1 or 2. $R^4$ represents a cyclic amino acid moiety of the general formula II, III or IV

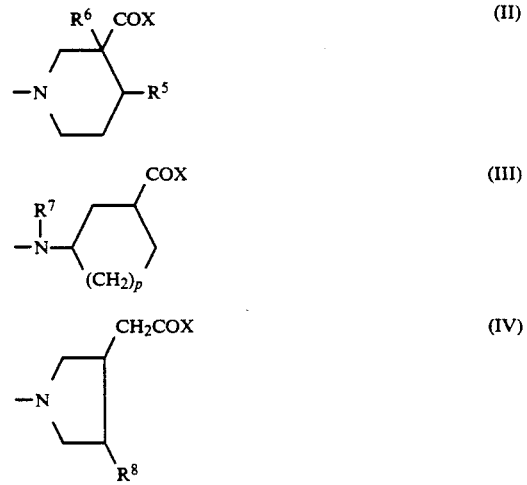

where p in formula III is 1 or 2, $R^5$ represents hydrogen or hydroxy, $R^6$ represents hydrogen or $R^5$ together with $R^6$ represents an additional bond, $R^7$ represents hydrogen or lower alkyl, $R^8$ represents hydrogen or hydroxy and X represents $-NH_2$ or $R^9$, in which $R^9$ represents hydroxy or alkoxy and pharmaceutically acceptable acid addition salts, and when $R^9$ is hydroxy also pharmaceutically acceptable metal salts and optionally alkylated ammonium salts thereof. The compounds of formula I have a greater lipophilicity—and thus a greater availability to the brain—as well as a far higher affinity to the GABA uptake sites compared to the parent amino acids, and they therefore possess interesting and useful pharmacological properties.

It has been demonstrated that the novel compounds of the general formula I exhibit GABA re-uptake inhibitory properties and possess useful pharmacological properties on the central nervous system, i.e. that they cause a selective enhancement of GABA'ergic activity. Compounds of formula 1 may be used to treat, for example, pain, anxiety. epilepsy and certain muscular and movement disorders. They may also find use as sedatives and hypnotics.

In formula I at least one of the nuclei $R^1$ and $R^2$ which are the same or different, and which may be optionally substituted, is preferably selected from the group consisting of furanyl, oxazolyl, phenyl, pyrazolyl, pyrazinyl, pyridazinyl, pyrimidinyl, pyrrolyl, thiazolyl, thienyl or 1,2,4-triazolyl, more preferred from the group consisting of phenyl, pyrrolyl, thiazolyl or thienyl.

In the definition of $R^1$ and $R^2$ furanyl is 2-furanyl or 3-furanyl; imidazolyl is 2-imidazolyl, 4-imidazolyl or 5-imidazolyl; oxazolyl is 2-oxazolyl, 4-oxazolyl or 5-oxazolyl; pyrazolyl is 3-pyrazolyl, 4-pyrazolyl or 5-pyrazolyl: pyrazinyl is 2-pyrazinyl or 3-pyrazinyl; pyridazinyl is 3-pyridazinyl, 4-pyridazinyl, 5-pyridazinyl or 6-pyridazinyl; pyridyl is 2-pyridyl, 3-pyridyl or 4-pyridyl; pyrimidyl is 2-pyrimidyl, 4-pyrimidyl or 5-pyrimidyl; pyrrolyl is 2-pyrrolyl; thiazolyl is 2-thiazolyl, 4-thiazolyl or 5-thiazolyl; thienyl is 2-thienyl or 3-thienyl and 1,2,4-triazolyl is 1,2,4-triazol-3-yl or 1,2,4-triazol-5-yl.

The substituents optionally chosen for the nuclei $R^1$ and/or $R^2$ are preferably lower alkylamino, lower alkylthio, lower alkoxy, amino, azido, cyano, halogen, hydroxy, lower alkyl or trifluoromethyl, more preferred lower alkylamino, lower alkoxy, amino, halogen or lower alkyl. The term halogen in this connection designates fluoro, chloro, bromo and iodo preferably fluoro, chloro and bromo, and more preferred fluoro and chloro.

Preferably $R^3$ is hydrogen, methyl or ethyl, more preferred $R^3$ is hydrogen.

Preferably $n+m=0$, 1 or 2, more preferred $n+m=1$.

$R^4$ preferably has a structure corresponding to formula II.

$R^5$ is preferably hydrogen or together with $R^6$ represents an additional bond.

$R^6$ is hydrogen or together with $R^5$ represents an additional bond.

$R^7$ is preferably hydrogen, methyl or ethyl, more preferred methyl.

$R^8$ is preferably hydrogen.

X is preferably $R^9$.

$R^9$ is hydroxy or alkoxy, preferably $R^9$ is hydroxy, methoxy or ethoxy; more preferred $R^9$ is hydroxy.

In the definition of the compounds of formula I the term lower alkyl when used alone—unless otherwise indicated—designates an alkyl group with not more than 4 carbon atoms, for example methyl, ethyl propyl, isopropyl cyclopropyl or tert-butyl, the preferred groups being methyl, ethyl and cyclopropyl. When used in combinations like alkoxy, alkylthio and alkylamino the term "lower alkyl" similarly designates an alkyl group with not more than 4 carbon atoms, preferably methyl and ethyl, so that the preferred combinations are methoxy, ethoxy, methylthio, ethylthio, methylamino and ethylamino respectively.

Examples of specific and preferred compounds of formula I are as follows:

(R)-Diphenylmethanone-O[2-(3-carboxypiperidin-1-yl)ethyl]oxime (1)

(R)-(2-Methylphenyl)-(3-methyl-2-thienyl)methanone O[2-(3-carboxypiperidin-1-yl)ethyl]oxime hydrochloride (2)

(R)-Bis(3-methyl-2-thienyl)methanone O-[2-(3-carboxypiperidin-1-yl)ethyl]oxime hydrochloride (3)

(R)-(2-Ethylphenyl)-(3-methyl-2-thienyl)methanone O-[2-(3-carboxypiperidin-1-yl)ethyl]oxime hydrochloride (4)

(R)-(3-Methyl-2-thienyl)-(2-thienyl)methanone O-[2-(3-carboxypiperidin-1-yl)ethyl]oxime (5)

(R)-(2-Methylphenyl)-(3-methyl-2-thienyl)methanone O-[2-(3-carboxypiperidin-1-yl)ethyl]oxime hydrochloride (10)

Diphenylmethanone O-[2-(3-carboxypiperidin-1-yl)ethyl]oxime hydrochloride (25)

(2-Methylphenyl)-(3-methyl-2-thienyl)methanone O-[2-(3-carboxypiperidin-1-yl)ethyl]oxime hydrochloride (26)

Diphenylmethanone O-[2-(3-carboxy-1,2,5,6-tetrahydropyridin-1-yl)ethyl]oxime (45)

(2-Methylphenyl)phenylmethanone O-[2-(3-carboxy-1,2,5,6-tetrahydropyridin-1-yl)ethyl]oxime hydrochloride (50)

(3-Fluorophenyl)-(2-methylphenyl)methanone O-[2-(3-carboxy-1,2,5,6-tetrahydropyridin-1-yl)ethyl]oxime hydrochloride (51)

(R)-Bis(4-fluoro-2-methylphenyl)methanone O-[2-(3-carboxypiperidin-1-yl)ethyl]oxime hydrochloride (53)

(2,4-Dichlorophenyl)-(3-methyl-2-thienyl)methanone O-[2-(3-carboxy-1,2,5,6-tetrahydropyridin-1-yl)ethyl]oxime hydrochloride (58)

Bis(2-methylphenyl)methanone O-[2-(3-carboxy-1,2,5,6-tetrahydropyridin-1-yl)ethyl]oxime hydrochloride (64)

(2-Chlorophenyl)phenyl-methanone O-[2-(3-ethoxycarbonyl1,2,5,6-tetrahydropyridin-1-yl)ethyl]oxime hydrochloride (76)

and other pharmaceutically-acceptable acid addition salts and metal salts and optionally alkylated ammonium salts thereof.

The compounds of formula I may exist as geometric and optical isomers and all isomers and mixtures thereof are included herein. Isomers may be separated by means of standard methods such as chromatographic techniques or fractional crystallization of salts with optically active acids or bases.

Pharmaceutically acceptable acid addition salts of compounds of formula I include those derived from inorganic or organic acids such as hydrochloric, hydrobromic, sulfuric, phosphoric, acetic, lactic, maleic, phthalic and fumaric acid.

The compounds having the general formula 1 may be prepared by the following conventional methods:

Method A:

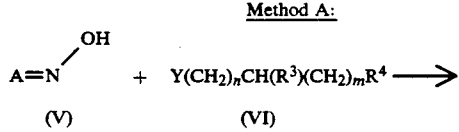

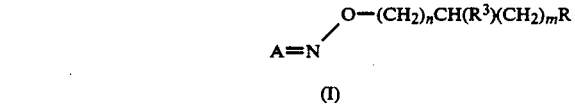

An oxime of formula V, wherein A is as defined above is reacted with a compound of formula VI, wherein $R^3$, $R^4$, n and m are as defined above, and y is a suitable leaving group such as halogen or p-toluenesulphonate. This reaction may be carried out in a polar, inert solvent, e.g. acetone, ethanol or N,N-dimethylformamide in the presence of a base, e.g. potassium carbonate or sodium hydride at a temperature up to reflux temperature for 1 to 72 h.

Method B:

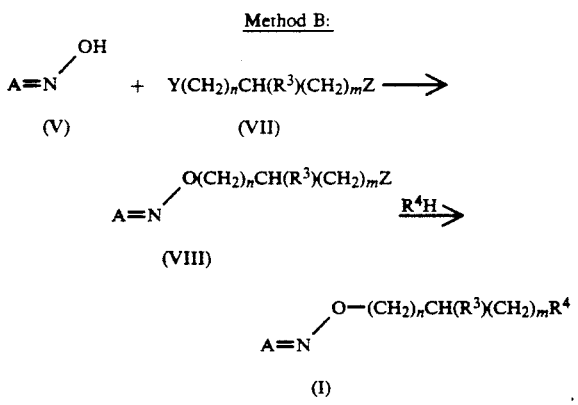

An oxime of formula V, wherein A is as defined above, is alkylated with a compound of formula VII, where Y is a suitable reactive leaving group, such as bromine or p-toluenesulphonate, and Z is a less labile group, e.g. chlorine (or alternatively a group such as hydroxy which may be converted into a reactive leaving group), and $R^3$, n and m are as defined above. This reaction may be carried out in a suitable solvent, e.g. acetone, ethanol or N,N-dimethylformamide in the presence of a base, e.g. potassium carbonate or sodium hydride at a temperature up to reflux temperature for 1 to 72 h.

The product VIII of this reaction wherein A, $R^3$, n, m and Z are as defined above, is reacted with $R^4H$, wherein $R^4$ is an amino acid or an amino acid derivative as specified above. This alkylation reaction may be carried out in an inert solvent, such as acetone, in the presence of a base e.g. potassium carbonate and a catalyst, e.g. an alkali metal iodide at a temperature up to reflux temperature for 1 to 96 h.

Method C:

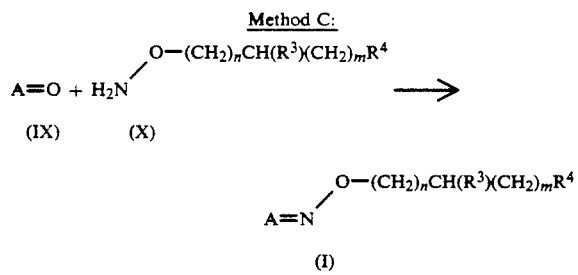

A ketone of formula IX, wherein A is as defined above, is reacted with an alkyl hydroxylamine of formula X, wherein $R^3$, $R^4$, n and m are as defined above in an inert solvent, e.g. ethanol or pyridine or a combination of solvents at a temperature up to reflux temperature for 0.5–12 h.

Under certain circumstances it may be necessary to protect e.g. the carboxy groups in the intermediates used in the above methods (e.g. $R^4H$, V or VI) with suitable protecting groups. In cases where A contains an amino group, this may be protected by acylation, and in the cases where A and/or $R^4$ contain a hydroxy group, this may be protected for example by acylation or by ether formation. The carboxylic acid group in $R^4$ can for example be esterified. Introduction and removal of such groups is described in "Protective Groups in Organic Chemistry" J. F. W. McOrnie ed. (New York, 1973).

If esters have been prepared in methods A–C, compounds of formula I where X is OH may be prepared by hydrolysis of the ester group, preferably at room temperature in a mixture of an aqueous alkali metal hydroxide solution and an alcohol such as methanol or ethanol, for about 0.5 to 6 h.

Compounds of formula V may be prepared by reacting the appropriate ketone or aldehyde with hydroxylamine (or its hydrochloride) in a solvent such as ethanol or pyridine (see e.g. W. E. Bachmann, *Org.Syn.*, (1967) 70; W. G. Honey et al., *J.Pharm.Sci.*, 66 (1977) 1602–1606; S. Rossi et al., *Farm. Ed.Sci.*, 24 (1969) 685–703 or P. L. Huerta et al., *J.Pharm. Sci.* 66 (1977) 1120–4.

Compounds of formula VI may be prepared by reaction of the appropriate amino acid ($R^4H$) protected for example as the ethyl ester with a 2-haloethanol e.g. 2-bromoethanol in the presence of a base, e.g. triethylamine or an alkali metal carbonate. The solvent may conveniently be ethanol, acetone, methyl ethyl ketone or N,N-dimethylformamide. This is followed by halogenation with a suitable halogenating agent in an inert solvent at reflux temperature for 0.5 to 24 h. The solvent may conveniently be toluene and the halogenating agent may for example be thionyl chloride.

Compounds of formula x may be prepared by O-alkylating e.g. acetone oxime with compound VI in a suitable solvent, such as benzene, pyridine or ethanol in the presence of a base, e.g. an alkali metal carbonate at for example reflux temperature for 0.5–24 h. This is followed by hydrolysis of the product under acidic conditions for example using 10% hydrochloric acid as solvent at reflux temperature for 0.5 to 24 h (see F. J. Villiani et al., *J.Pharm.Sci.*, 58 (1969) 138–141; G. Aichinger et al., *Arznem.Forsch.*, 19 (1969) 838–845).

Pharmacological Methods

The in vitro inhibition of [$^3$H]-GABA uptake was assessed essentially by the method of Fjalland (*Acta Pharmacol. Toxicol.* 42 (1978) 73–76).

Male Wistar rat cortical tissue was gently homogenized by hand using a glass teflon homogenizer in 10 volumes of 0.32M sucrose. Incubation was performed in a 40 mM tris HCl buffer (pH 7.5 at 30° C.) containing 120 nM NaCl, 9.2 nM KCl, 4 mM $MgSO_4$, 2.3 mM $CaCl_2$ and 10 mM glucose, for 60 min. at 30° C. Ligand concentration was 0.2 nM.

Values for inhibition of GABA uptake for some compounds of the invention are recorded below.

Results obtained—inhibition of [$^3$H]-GABA uptake

| Example | $IC_{50}$ (nm) in vitro |
|---|---|
| 1 | 82 |
| 2 | 44 |
| 3 | 30 |
| 4 | 52 |
| 5 | 64 |
| 25 | 138 |
| 26 | 58 |
| 45 | 48 |
| 46 | 59 |
| 47 | 51 |
| 83 | 217 |

Compounds of formula I are useful because they possess pharmacological activity in man. In particular the compounds of formula I are useful as inhibitors of GABA uptake.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent. No toxic effects have been observed.

The compounds of formula I may be administered in pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmacaeutical carrier or diluent. The compositions of this invention may be prepared by conventional techniques or appear in conventional forms, for example capsules or tablets.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or in the form of a troche or lozenge. The amount of solid carrier will vary widely but will usually be from about 25 mg to about 1 g. If a liquid carrier is used, the preparation may appear in the form of a syrup, emulsion, soft gelatin capsule or sterile injectable liquid such as an aqueous or nonaqueous liquid suspension.

The pharmaceutical compositions of this invention can be made following the conventional techniques of the pharmaceutical industry involving mixing, granulating and compressing or variously mixing and dissolving the ingredients as appropriate to give the desired end product.

The route of administration may be any route which effectively transports the active compound to the appropriate or desired place, such as oral or parenteral, the oral route being preferred.

The features disclosed in the above specification and in the following examples and claims may, both separately and in any combination thereof, be material for realizing this invention in diverse forms thereof.

The process for preparing compounds of formula I and preparations containing them is further illustrated in the following examples. The examples illustrate some preferred embodiments.

Hereinafter, tlc is thin layer chromatography, THF is tetrahydrofuran, DMF is N,N-dimethylformamide, and m.p. is melting point. The structures of the compounds are confirmed by NMR and elemental analysis. Where melting points are given, these are uncorrected. All temperatures are in °C. Compounds used as starting materials are either known compounds or compounds which can readily be prepared by methods known per se. Column chromatography was carried out using the technique described by W. C. Still et al., *J.Org.Chem.*, 43 (1978) 2923–2925 on Merck kieselgel 60 (Art. 9385) silica gel.

EXAMPLE 1 (METHOD A)

(R)-Diphenylmethanone O-[2-(3-carboxypiperidin-1-yl)ethyl]oxime

The (R)-enantiomer of ethyl nipecotate (100 g, 0.64 mol) (A. M. Akkerman et al., *Rec.Trav.Chim.*, 70 (1951), 899; G. Bettoni et al., *Gazz.Chim.Ital.*, 102 (1972) 189) was mixed in dry acetone (300 ml) with 2-bromoethanol (84.98 g, 0.68 mol), dried, powdered potassium carbonate (176.91 g, 1.28 mol) and potassium iodide (21.58 g, 0.13 mol). The reaction mixture was stirred at room temperature for 18 h and at reflux for 24 h. Filtration and evaporation of the filtrate gave an oil which was purified by distillation in vacuo (110°–115° C., 0.1 mmHg), yield 72.17 g (56%). Tlc rf 0.20 ($SiO_2$; dichloromethane/methanol 19/1).

The above alcohol (19.86 g, 0.099 mol) was dissolved in toluene (125 ml). A solution of thionyl chloride (14.16 g, 0.119 mol) in toluene (50 ml) was added dropwise and the reaction mixture was stirred at room temperature for 2 h. Cooling in an icebath followed by filtration provided the (R)-N-(2-chloroethyl)nipecotic acid ethyl ester as a solid. A sample was recrystallized from 2-propanol, m.p. 187.5°–194.5° C.

To the above ester hydrochloride (2.56 g, 10 mmol), dried, powdered potassium carbonate (5.53 g, 40 mmol), acetone (200 ml) and benzophenone oxime (3.94 g, 20 mmol) was added. The suspension was heated at reflux for 96 h, cooled and filtered. The solvent was removed from the filtrate in vacuo to give a residue. Water (100 ml) and ethyl acetate (100 ml) were introduced. The aqueous layer was separated and further extracted with ethyl acetate (2×100 ml). The combined organic extracts were dried ($MgSO_4$) and evaporated to give a brown oil (6.2 g). This oil was purified by "flash" chromatography eluting with cyclohexane/ethyl acetate (5/1) to provide the (R)-diphenylmethanone O-[2-(3-ethoxycarbonylpiperidin-1-yl)ethyl]oxime (2.66 g, 70%) as a gum, tlc rf 0.067 ($SiO_2$, cyclohexane/ethyl acetate 5/1).

The above ester (2.66 g, 6 99 mmol) was dissolved in ethanol (100 ml) and 10N sodium hydroxide solution (6.99 ml) was introduced. After 2 h at room temperature the solution was cooled in an ice bath and the pH was adjusted to 3 with 4 N hydrochloric acid. Extraction with dichloromethane (3×50 ml), drying ($MgSO_4$) of the combined fractions and evaporation provided the title compound as a hydrochloride, hydrate (1.3 g, 53%) m.p. 241°–242° C.

By the above general procedure the following oxime derivatives were prepared:

EXAMPLE 2

(R)-(2-Methylphenyl)-(3-methyl-2-thienyl)methanone O-[2-(3-carboxypiperidin-1-yl)ethyl]oxime hydrochloride Tlc rf 0.30 ($SiO_2$, dichloromethane/methanol 1/1).

EXAMPLE 3

(R)-Bis(3-methyl-2-thienyl)methanone
O-[2-(3-carboxypiperidin-1-yl)ethyl]oxime
hydrochloride M.p. 45° C.

EXAMPLE 4

(R)-(2-Ethylphenyl)-(3-methyl-2-thienyl)methanone
O-[2-(3-carboxypiperidin-1-yl)ethyl]oxime
hydrochloride M.p. 202°–203° C. (acetone).

EXAMPLE 5

(R)-(3-Methyl-2-thienyl)-(2-thienyl)methanone
O-[2-(3-carboxypiperidin-1-yl)ethyl]oxime M.p. 210°–216° C.

EXAMPLE 6

(R)-(3-Methoxyphenyl)-(3-methyl-2-thienyl)methanone
O-[2-(3-carboxypiperidin-1-yl)ethyl]oxime
hydrochloride Tlc rf 0.3 (SiO$_2$, dichloromethane/methanol 1/1)

EXAMPLE 7

(R)-(2-Methylphenyl)-(1-methyl-2-pyrrolyl)methanone
O-[2-(3-carboxypiperidin-1-yl)ethyl]oxime Tlc rf 0.29 (SiO$_2$, dichloromethane/methanol 1/1).

EXAMPLE 8

(R)-(1-Ethyl-2-pyrrolyl)phenylmethanone
O-[2-(3-carboxypiperidin-1-yl)ethyl]oxime
hydrochloride M.p. 221.5°–225° C.

EXAMPLE 9

(R)-(3-Methoxyphenyl)-(4-methyl-2-thienyl)methanone
O-[2-(3-carboxypiperidin-1-yl)ethyl]oxime
hydrochloride Tlc, rf 0.31 (SiO$_2$, dichloromethane/methanol 1/1).

EXAMPLE 10

(R)-(2-Methylphenyl)-(3-methyl-2-thienyl)methanone
O-[2-(3-carboxypiperidin-1-yl)ethyl]oxime
hydrochloride Tlc, rf 0.32 (SiO$_2$, dichloromethane/methanol 1/1).

EXAMPLE 11

(R)-(2-methyl-1,2,4-triazol-3-yl)-(2-thienyl)methanone
O-[2-(3-carboxypiperidin-1-yl)ethyl]oxime
hydrochloride Tlc, rf 0.90 (reversed phase, Whatman KCl 8F, methanol/water 4/1).

EXAMPLE 12

(R)-(2-Methyl-1,2,4-triazol-3-yl)-(2-thienyl)methanone
O-[2-(3-carboxypiperidin-1-yl)ethyl]oxime
hydrochloride Tlc, rf 0.90 (reversed phase, Whatman KCl 8F, methanol/water 4/1).

EXAMPLE 13

(R)-(3-Azidophenyl)-(3-methyl-2-thienyl)methanone
O-[2-(3-carboxypiperidin-1-yl)ethyl]oxime
hydrochloride Tlc, rf 0.20 (SiO$_2$, methanol).

EXAMPLE 14

(R)-(2-Methylphenyl)-(3-methyl-2-thienyl)methanone
O-[2-(3-ethoxycarbonylpiperidin-1-yl)ethyl]oxime Tlc, rf 0.35 (SiO$_2$, cyclohexane/ethylacetate 1/1).

EXAMPLE 15

(R)-(2-Azidophenyl)phenylmethanone
O-[2-(3-carboxypiperidin-1-yl)ethyl]oxime
hydrochloride Tlc, rf 0.14 (SiO$_2$, dichloromethane/methanol 1/1).

EXAMPLE 16

(S)-Diphenylmethanone
O-[2-(3-carboxypiperidin-1-yl)ethyl]oxime
hydrochloride

Tlc, rf 0.38 (SiO$_2$, dichloromethane/methanol 1/1).

EXAMPLE 17

(R)-Bis(3-ethyl-2-thienyl)methanone
O-[2-(3-carboxypiperidin1-yl)ethyl]oxime
hydrochloride Tlc, rf 0.30 (SiO$_2$, dichloromethane/methanol 1/1).

EXAMPLE 18

(R)-(2,4-Dichlorophenyl)-(3-methyl-2-thienyl)methanone O-[2-(3-carboxypiperidin-1-yl)ethyl]oxime
hydrochloride Tlc, rf 0.52 (SiO$_2$, dichloromethane/methanol 1/1).

EXAMPLE 19

(R)-(3-Methoxyphenyl)phenylmethanone
O-[2-(3-carboxypiperidin-1-yl)ethyl]oxime
hydrochloride Mp 180°–185° C.

EXAMPLE 20

(R)-(3-Methoxyphenyl)-(2-methoxyphenyl)methanone
O-[2-(3-carboxypiperidin-1-yl)ethyl]oxime Mp 185°–190° C.

EXAMPLE 21

(R)-Bis(4-chloro-2-methylphenyl)methanone
O-[2-(3-carboxypiperidin-1-yl)ethyl]oxime
hydrochloride Mp 230°–232° C.

EXAMPLE 22

(R)-(2-Methylphenyl)-(3-methyl-2-thienyl)methanone
O-[2-(3-ethoxycarbonylpiperidin-1-yl)ethyl]oxime
hydrochloride Mp 124°–125.5° C.

EXAMPLE 23

(R)-(4-Chloro-2-methylphenyl)-(3-methyl-2-thienyl)-methanone O-[2-(3-carboxypiperidin-1-yl)ethyl]oxime hydrochloride Mp 170°-175° C.

EXAMPLE 24

(R)-Bis(2-methylphenyl)methanone O-[2-(3-carboxypiperidin-1-yl)ethyl]oxime hydrochloride Tlc, rf. 0.49 (SiO$_2$, dichloromethane/methanol 1/1).
Using (R,S)-N-(2-chloroethyl)nipecotic acid ethyl ester as a starting material the following (R,S)-enantiomeric mixtures were prepared (according to method A, Example 1):

EXAMPLE 25

Diphenylmethanone O-[2-(3-carboxypiperidin-1-yl)ethyl]oxime hydrochloride

M.p. 234°-235° C.

EXAMPLE 26

(2-Methylphenyl)-(3-methyl-2-thienyl)methanone O-[2-(3-carboxypiperidin-1-yl)ethyl]oxime hydrochloride Tlc rf. 0.30 (SiO$_2$, dichloromethane/methanol 1/1).

EXAMPLE 27

(1-Methyl-2-imidazolyl)phenylmethanone O-[2-(3-carboxypiperidin-1-yl)ethyl]oxime Tlc rf 0.07 (SiO$_2$; methanol/dichloromethane 1/1).

EXAMPLE 28

Phenyl-(2-pyridyl)methanone O-[2-(3-carboxypiperidin-1-yl)ethyl]oxime hydrochloride M.p. 61°-63° C.

EXAMPLE 29

Phenyl-(2-pyrrolyl)methanone O-[2-(3-carboxypiperidin-1-yl)ethyl]oxime hydrochloride M.p. 172.5°-176° C.

EXAMPLE 30

Bis(4-chlorophenyl)methanone O-[2-(3-carboxypiperidin-1-yl)ethyl]oxime hydrochloride Tlc rf 0.25 (SiO$_2$, dichloromethane/methanol 1/1).

EXAMPLE 31

(3-Azidophenyl)phenylmethanone O-[2-(3-carboxypiperidin-1-yl)ethyl]oxime hydrochloride Tlc, rf. 0.30 (SiO$_2$, methanol).

EXAMPLE 32

(4-Fluorophenyl)phenylmethanone O-[2-(3-carboxypiperidin-1-yl)ethyl]oxime hydrochloride Tlc, rf. 0.35 (SiO$_2$, dichloromethane/methanol 1/1).

EXAMPLE 33

(2-Chlorophenyl)phenylmethanone O-[2-(3-carboxypiperidin-1-yl)ethyl]oxime hydrochloride Tlc, rf. 0.35 (SiO$_2$, dichloromethane/methanol 1/1).

EXAMPLE 34

(4-Chloro-2-methylphenyl)-(2-methylphenyl)methanone O-[2-(3-carboxypiperidin-1-yl)ethyl]oxime hydrochloride Tlc, rf. 0.33 (SiO$_2$, dichloromethane/methanol 1/1).

EXAMPLE 35

(3-Azidophenyl)phenylmethanone O-[2-(3-carboxypiperidin-1-yl)ethyl]oxime hydrochloride Tlc, rf. 0.30 (SiO$_2$, methanol).

EXAMPLE 36

(3-Nitrophenyl)phenylmethanone O-[2-(3-carboxypiperidin-1-yl)ethyl]oxime hydrochloride Tlc, rf. 0.30 (SiO$_2$, methanol).

EXAMPLE 37

Bis(2-hydroxyphenyl)methanone O-[2-(3-carboxypiperidin-1-yl)ethyl]oxime hydrochloride Mp 215°-220° C. (not recrystallised).

EXAMPLE 38

Bis(3-methoxyphenyl)methanone O-[2-(3-carboxypiperidin-1-yl)ethyl]oxime hydrochloride Tlc, rf. 0.31 (SiO$_2$, dichloromethane/methanol 1/1).

EXAMPLE 39

(2,4-Dichlorophenyl)-(3-methyl-2-thienyl)methanone O-[2-(3-carboxypiperidin-1-yl)ethyl]oxime hydrochloride Tlc, rf. 0.30 (SiO$_2$, dichloromethane/methanol 1/1).

EXAMPLE 40

(2-Chlorophenyl)-(2-methylphenyl)methanone O-[2-(3-carboxypiperidin-1-yl)ethyl]oxime hydrochloride Tlc, rf. 0.57 (SiO$_2$, dichloromethane/methanol 1/1).

EXAMPLE 41

(2-Methylphenyl)-(3-methylphenyl)methanone O-[2-(3-carboxypiperidin-1-yl)ethyl]oxime hydrochloride Mp 174°-176° C.

EXAMPLE 42

(2-Methylphenyl)-(3-methyl-2-thienyl)methanone O-[2-(3-carboxypiperidin-1-yl)ethyl]oxime hydrochloride Mp 209°-211° C.

EXAMPLE 43

(3-Hydroxyphenyl)phenylmethanone
O-[2-(3-carboxypiperidin-1-yl)ethyl]oxime
hydrochloride Tlc, rf. 0.40 (SiO$_2$, methanol).

EXAMPLE 44

Bis(2-methylphenyl)methanone
O-[2-(3-carboxypiperidin-1-yl)-1-methylethyl]oxime
hemihydrochloride Tlc, rf. 0.52 (reversed phase, Whatman KCl 8F, methanol/water 4/1).

EXAMPLE 45 (Method B)

Diphenylmethanone
O-[2-(3-carboxy-1,2,5,6-tetrahydropyridin-1-yl)ethyl]oxime

Benzophenone oxime (3.94 g, 20 mmol), 1-bromo-2-chloroethane (28.7 g, 200 mmol) a nd dried, powdered potassium carbonate (5.53 g, 80 mmol) in acetone (60 ml) were heated at reflux for 72 h. The reaction mixture was cooled and filtered and the filtrate was evaporated to an oily residue which was purified by "flash" chromatography (eluting with heptane/ethyl acetate 19/1) to provide diphenylmethanone O-(2-chloroethyl)oxime (3.82 g, 73%) as an oil, tlc rf 0.36 (SiO$_2$, heptane/ethyl acetate 9/1).

The above chloroethyloxime (1.309 g, 5 mmol) was dissolved in acetone (25 ml) and guvacine methyl ester hydrochloride (1.776 g, 1o mmol) powdered, dried potassium carbonate (2.073 g, 15 mmol) and potassium iodide (0.75 g, 5 mmol) were introduced. The reaction mixture was heated at reflux for 18 h and cooled. Filtration and evaporation of the filtrate provided an oil which was purified by flash chromatography on silica gel, eluting with cyclohexane/ethyl acetate (2/1) to provide diphenylmethanone O-[2-(3-methoxycarbonyl-1,2,5,6-tetrahydropyridin-1-yl)ethyl]oxime (0.87 g, 48%) as a gum, tlc rf 0.30 (SiO$_2$, heptane/ethyl acetate 1/1). Starting diphenylmethanone, O-(2-haloethyl)oxime (0.66 g, 50%) was also isolated.

The above methyl ester (0.81 g, 2.39 mmol) was dissolved in ethanol (25 ml) And 10N sodium hydroxide solution (2.39 ml) was added. The solution was stirred at room temperature for 4 h and acidified to pH 2 with 2N hydrochloric acid. The liquid was extracted with dichloromethane (3×50 ml) and the combined organic extracts were dried (MgSO$_4$). Evaporation of the solvent gave a gum which was freeze-dried to give the title compound (0.825 g, 89%) as a hemi hydrochloride.

Tlc rf 0.40 (SiO$_2$, dichloromethane/methanol 1/1). Found: C, 65.6; H, 6.3; N, 7.05; Cl, 4.9. C$_{21}$H$_{22}$N$_2$O$_3$. ½HCl.H$_2$O requires C, 65.2; H, 6.4; N, 7.2; Cl, 4.6%.

By the above general procedure (Example 45 Method B) the following oxime derivatives were prepared:

EXAMPLE 46

Bis(3-methyl-2-thienyl)methanone
O-[2-(3-carboxy-1,2,5,6-tetrahydropyridin-1-yl)ethyl]oxime hydrochloride M.p. 79°–80° C.

EXAMPLE 47

(S)-Bis(3-methyl-2-thienyl)methanone
O-[2-(3-carboxypiperidin-1-yl)ethyl]oxime
hydrochloride M.p. 168°–169° C.

EXAMPLE 48

(S)-(2-Methylphenyl)-(3-methyl-2-thienyl)methanone
O-[2-(3-carboxypiperidin-1-yl)ethyl]oxime
hydrochloride Tlc rf 0.30 (SiO$_2$, dichloromethane/methanol 1/1).

EXAMPLE 49

(3-Methyl-2-thienyl)-(2-thienyl)methanone
O-[2-(3-carboxy-1,2,5,6-tetrahydropyridin-1-yl)ethyl]oxime hydrochloride Tlc rf 0.8 (reversed phase, Whatman KC18F, methanol/water (4/1).

EXAMPLE 50

(2-Methylphenyl)phenylmethanone
O-[2-(3-carboxy-1,2,5,6-tetrahydropyridin-1-yl)ethyl]oxime hydrochloride Tlc, rf. 0.49 (SiO$_2$, dichloromethane/methanol 1/1).

EXAMPLE 51

(3-Fluorophenyl)-(2-methylphenyl)methanone
O-[2-(3-carboxy-1,2,5,6-tetrahydropyridin-1-yl)ethyl]oxime hydrochloride M.p. 219°–223° C.

EXAMPLE 52

(R)-Bis(4-fluoro-2-methylphenyl)methanone
O-[2-(3-ethoxycarbonylpiperidin-1-yl)ethyl]oxime
hydrochloride M.p. 102°–103° C.

EXAMPLE 53

(R)-Bis(4-fluoro-2-methylphenyl)methanone
O-[2-(3-carboxypiperidin-1-yl)ethyl]oxime
hydrochloride M.p. 181°–182° C.

EXAMPLE 54

(2-Methylphenyl)-(3-methyl-2-thienyl)methanone
O-[2-(3-ethoxycarbonyl-1,2,5,6-tetrahydropyridin-1-yl)ethyl]oxime hydrochloride M.p. 116°–117° C.

EXAMPLE 55

(2-Methylphenyl)-(3-methyl-2-thienyl)methanone
O-[2-(3-carboxy-1,2,5,6-tetrahydropyridin-1-yl)ethyl]oxime hydrochloride M.p. 204°–207° C.

EXAMPLE 56

Bis(4-fluoro-2-methylphenyl)methanone
O-[2-(3-ethoxycarbonyl-1,2,5,6-tetrahydropyridin-1-yl)ethyl]oxime hydrochloride M.p. 157°–159° C.

EXAMPLE 57

Bis(4-fluoro-2-methylphenyl)methanone O-[2-(3-carboxy-1,2,5,6-tetrahydropyridin-1-yl)ethyl]oxime hydrochloride M.p. 241°-244° C.

EXAMPLE 58

(2,4-Dichlorophenyl)-(3-methyl-2-thienyl)methanone O-[2-(3-carboxy-1,2,5,6-tetrahydropyridin-1-yl)ethyl]oxime hydrochloride Tlc, rf. 0.76 (reversed phase, Whatman KCl 8F, methanol/water 4/1).

EXAMPLE 59

(2-Chlorophenyl)-(2-methylphenyl)methanone O-[2-(3-carboxy-1,2,5,6-tetrahydropyridin-1-yl)ethyl]oxime hydrochloride M.p. 152°-155° C.

EXAMPLE 60

(2-Methylphenyl)-(3-trifluoromethylphenyl)methanone O-[2-(3-carboxy-1,2,5,6-tetrahydropyridin-1-yl)ethyl]oxime hydrochloride M.p. 205°-207° C.

EXAMPLE 61

(R)-(2-Methylphenyl)-(3-trifluoromethylphenyl)methanone O-[2-(3-carboxypiperidin-1-yl)ethyl]oxime hydrochloride M.p 156°-158° C.

EXAMPLE 62

E/Z-2-(2-Methylphenyl)-2-(2-methyl-4-trifluoromethylphenyl)acetaldehyde O-[2-(3-carboxy-1,2,5,6-tetrahydropyridin-1-yl)ethyl]oxime hydrochloride M.p. 195°-200° C.

EXAMPLE 63

(S)-(2-Methylphenyl)-(3-methyl-2-thienyl)methanone O-[2-(3-ethoxycarbonylpiperidin-1-yl)ethyl]oxime hydrochloride Tlc, rf. 0.35 (SiO2, cyclohexane/ethylacetate 1/1).

EXAMPLE 64

Bis(2-methylphenyl)methanone O-[2-(3-carboxy-1,2,5,6-tetrahydropyridin-1-yl)ethyl]oxime hydrochloride M.p. 214°-218.5° C.

EXAMPLE 65

(S)-Bis(2-methylphenyl)methanone O-[2-(3-carboxypiperidin1-yl)ethyl]oxime hydrochloride Tlc, rf. 0.39 (SiO2, dichloromethane/methanol 1/1).

EXAMPLE 66

Diphenylmethanone O-[2-(3-aminocarbonylpiperidin-1-yl)ethyl]oxime

Tlc, rf. 0.41 (SiO2, dichloromethane/methanol 9/1).

EXAMPLE 67

(4-Chloro-2-methylphenyl)-(2-methylphenyl)methanone O-[2-(3-carboxy-1,2,5,6-tetrahydropyridin-1-yl)ethyl]oxime hydrochloride Tlc, rf. 0.45 (SiO2, dichloromethane/methanol 1/1).

EXAMPLE 68

(2-Chlorophenyl)phenylmethanone O-[2-(3-carboxy-1,2,5,6-tetrahydropyridin-1-yl)ethyl]oxime hydrochloride M.p. 198.5°-200° C.

EXAMPLE 69

(2-Thienyl)phenylmethanone O-[2(3-carboxy-1,2,5,6-tetrahydropyridin-1-yl)ethyl]oxime hydrochloride Tlc, rf. 0.63 (SiO2, dichloromethane/methanol 1/1).

EXAMPLE 70

(3-Chlorophenyl)-(2-methylphenyl)methanone O-[2-(3-carboxy-1,2,5,6-tetrahydropyridin-1-yl)ethyl]oxime hydrochloride M.p. 223° C. (dec).

EXAMPLE 71

(3-Methoxyphenyl)phenylmethanone O-[2-(3-carboxy-1,2,5,6-tetrahydropyridin-1-yl)ethyl]oxime hydrochloride M.p. 140°-145° C.

EXAMPLE 72

(3-Methoxyphenyl)-(2-methylphenyl)methanone O-[2-(3-carboxy-1,2,5,6-tetrahydropyridin-1-yl)ethyl]oxime hydrochloride M.p. 190°-195° C.

EXAMPLE 73

(4-Fluoro-2-methylphenyl)-(2-methylphenyl)methanone O-[2-(3-carboxy-1,2,5,6-tetrahydropyridin-1-yl)ethyl]oxime hydrochloride M.p. 205°-213° C.

EXAMPLE 74

Diphenylmethanone O-[2-(3-ethoxycarbonyl-1,2,5,6-tetrahydropyridin-1-yl)ethyl]oxime hydrochloride M.p. 110°-116° C. (toluene/cyclohexane).

EXAMPLE 75

(2-Fluorophenyl)-(2-methylphenyl)methanone O-[2-(3-carboxy-1,2,5,6-tetrahydropyridin-1-yl)ethyl]oxime hydrochloride M.p. 195°-196° C. (dec).

EXAMPLE 76

(2-Chlorophenyl)phenylmethanone O-[2-(3-ethoxycarbonyl-1,2,5,6-tetrahydropyridin-1-yl)ethyl]oxime hydrochloride Tlc, rf. 0.25 (SiO2, cyclohexane/ethylacetate 1/1).

EXAMPLE 77

Bis(2-methylphenyl)methanone
O-[2-(3-ethoxycarbonyl-1,2,5,6-tetrahydropyridin-1-yl)ethyl]oxime hydrochloride M.p. 163°-164.5° C. (toluene/cyclohexane).

EXAMPLE 78

(4-Chloro-2-methylphenyl)-(3-methyl-2-thienyl)methanone
O-[2-(3-carboxy-1,2,5,6-tetrahydropyridin-1-yl)ethyl]oxime hydrochloride M.p. 213°-216° C.

EXAMPLE 79

(4-Fluoro-2-methylphenyl)-(3-methyl-2-thienyl)methanone
O-[2-(3-carboxy-1,2,5,6-tetrahydropyridin-1-yl)ethyl]oxime hydrochloride M.p. 165°-169° C.

EXAMPLE 80

(3,4-Dichlorophenyl)-(2-methylphenyl)methanone
O-[2-(3-carboxy-1,2,5,6-tetrahydropyridin-1-yl)ethyl]oxime hydrochloride M.p. 258°-260° C.

EXAMPLE 81

Bis(2-ethylphenyl)methanone
O-[2-(3-carboxy-1,2,5,6-tetrahydropyridin-1-yl)ethyl]oxime hydrochloride M.p. 130°-135° C.

EXAMPLE 82 (METHOD A)

(R,S)-Diphenylmethanone
O-[3-(3-carboxypiperidin-1-yl)propyl]oxime hydrochloride (R,S)-ethyl nipecotate (15.72 g, 100 mmol) was mixed in dry acetone (120 ml) with 3-bromo-1-propanol (2085 g, 150 mmol) and dried, powdered potassium carbonate (20.73 g, 150 mmol). The reaction mixture was heated at reflux for 3 h, cooled and filtered. The filtrate was evaporated to an oil (32.8 g) which was dissolved in dichloromethane. To this solution phosphorous tribromide (30.45 g, 112.5 mmol) was introduced dropwise maintaining reflux during addition, and when this was complete reflux was continued for 2.5 h. After cooling dry methanol (30 ml) was added and the mixture was poured into a mixture of saturated sodium bicarbonate solution (250 ml) and water (250 ml). The dichloromethane layer was separated and the aqueous layer was extracted with ethyl acetate (2×150 ml). The combined organic extracts were dried (MgSO$_4$) and evaporated to an oil which was purified by "flash" chromatography. Elution with cyclohexane/tetrahydrofuran 3/1 provided N-(3-bromopropyl)nipecotic acid ethyl ester (7.85 g, 28%) as a waxy solid. Found C, 47.3; H, 7.9; N, 4.7. $C_{11}H_{20}BrNO_2 \cdot 0.2\ H_2O$ required C, 46.9; H, 7.2; N, 4.95%.

This compound was used to alkylate benzophenone oxime, as outlined in Example 1, and the subsequent ester was hydrolysed to provide the title compound as a gummy solid (0.5 g, 52% from N-(3-bromopropyl)nipecotic acid ethyl ester). Tlc rf 0.70 (reversed phase, Whatman KC 18F, methanol/water 8/2).

Using (R)-N-(2-bromoethyl)nipecotic acid ethyl ester hydrobromide and an 2,2-diarylacetaldehyde oxime as starting materials the following compounds were prepared (according to method A, Example 1).

EXAMPLE 83

E/Z-(R)-2,2-Diphenylacetaldehyde
O-[2-(3-carboxy-piperidin-1- yl)ethyl]oxime hydrochloride rf. 0.34 (SiO$_2$, dichloromethane/methanol 1/1)

EXAMPLE 84

E/Z-(R)-2-(2-Methylphenyl)-2-phenylacetaldehyde
O-[2-(3-carboxypiperidin-1-yl)ethyl]oxime hydrochloride rf. 0.40 (SiO$_2$, dichloromethane/methanol 1/1).

EXAMPLE 85

E/Z-(R)-2-(2-Methylphenyl)-2-(2-methyl-4-trifluoromethylphenyl)acetaldehyde
O-[2-(3-carboxy-piperidin-1-yl)ethyl]oxime hydrochloride M.p. 190°-200° C.

EXAMPLE 86

Preparation of Capsules

| Ingredients | mg per capsule |
|---|---|
| (R)-diphenylmethanone O-[2-(3-carboxypiperidin-1-yl)ethyl]oxime | 10 |
| Magnesium stearate | 0.15 |
| Lactose | 15 |

The above ingredients are thoroughly mixed and placed in hard gelatin capsules. Such capsules are administered orally to subjects in need of treatment from 1-5 times daily.

EXAMPLE 87

Preparation of Tablets

| Ingredients | mg per tablet |
|---|---|
| (R)-diphenylmethanone O-[2-(3-carboxypiperidin-1-yl)ethyl]oxime | 200 |
| Corn starch | 50 |
| Polyvinyl pyrrolidine | 15 |
| Magnesium stearate | 1 |

The oxime is thoroughly mixed with two thirds of the corn starch and granulated. The granules obtained are dried, mixed with the remaining ingredients and compressed into tablets.

The capsules or tablets thus prepared are administered orally. Similarly, other oximes of formula I can be used.

We claim:

1. An O-substituted oxime of the formula I

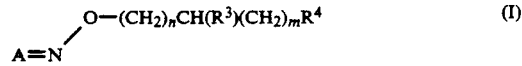

wherein

-continued

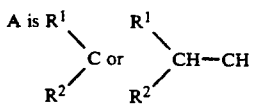

wherein at least one of $R^1$ and $R^2$, represents an aromatic moiety selected from the group consisting of imidazolyl, phenyl, pyrrolyl, pyridinyl, and the other represents phenyl, each ring optionally being substituted by one, two or three substituents selected from the group consisting of lower alkylamino, lower alkylthio, lower alkoxy, amino, azido, cyano, halogen, hydroxy, lower alkyl, nitro, mercapto and trifluoromethy; $R^3$ represents hydrogen or lower alkyl; n and m are numbers from 0 to 2; $R^4$ represents a cyclic amino acid moiety of formula II where p in formula III

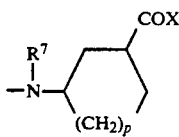

is 1 or 2; $R^7$ represents hydrogen or lower alkyl; and X represents NH or $R^9$, in which $R^9$ represents hydroxy or alkoxy, or of pharmaceutically-acceptable acid addition salt thereof or, and, when $R^9$ represents hydroxy, a pharmaceutically-acceptable metal salt thereof or an optionally-substituted ammonium salt thereof.

2. A compound, according to claim 1, wherein both $R^1$ and $R^2$ are oxazolyl, phenyl, or each ring optionally being substituted with one, two or three substituents selected from the group consisting of lower alkylamino, lower alkylthio, lower alkoxy, amino, azido, cyano, fluoro, chloro, bromo, iodo, hydroxy and lower alkyl.

3. A compound, according to claim 1, wherein $R^3$ represents hydrogen, methyl or ethyl.

4. A compound, according to claim 1, wherein n is 0, 1 or 2.

5. A compound, according to claim 1, wherein m is 0, 1, or 2.

6. A compound, according to claim 1 wherein $R^4$ is a group of the formula III

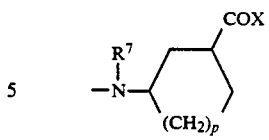

wherein $R^7$ is hydrogen or lower alkyl, preferably hydrogen, methyl or ethyl, p is 1 or 2 and X is $-NH_2$ or $R^9$ where $R^9$ is hydroxy or alkoxy.

7. Compound according to claim 1 wherein both $R^1$ and $R^2$ are phenyl substituted with one, two, or three substituents selected from the group consisting of lower-alkylamino, lower alkylthio, lower-alkoxy, amino, azido, cyano, fluoro, chloro, bromo, iodo, hydroxy, and lower-alkyl.

8. Compound according to claim 7 wherein the substituents are selected from lower-alkylamino, lower-alkoxy, amino, fluoro, chloro, and lower-alkyl.

9. Compound according to claim 1 wherein the substituents are selected from $C_{1-6}$-alkyl, $C_{1-6}$-alkoxy, azido, cyano, halogen, nitro, and hydroxy.

10. Compound according to claim 1 wherein $R^1$ is imidazolyl and $R^2$ is phenyl.

11. Compound according to claim 1 wherein $R^1$ is pyridinyl and $R^2$ is phenyl.

12. A compound according to claim 2, wherein the optional ring substituents are selected from the group consisting of lower alkylamino, lower alkoxy, amino, fluoro, chloro, and lower alkyl.

13. A compound according to claim 1, wherein $R^3$ represents hydrogen or methyl.

14. A compound according to claim 4 wherein n is 0 or 1.

15. A compound according to claim 5 wherein m is 0 or 1.

16. A compound according to claim 6 wherein $R^9$ is hydroxy, methoxy, or ethoxy.

17. A compound of claim 1 wherein $R^1$ is pyrrolyl and $R^2$ is phenyl.

18. Pharmaceutical composition suitable for treatment of a condition requiring an increased concentration of gamma-aminobutyric acid containing an effective GABA re-uptake inhibitory amount of a compound of claim 1 in association with a pharmaceutically-acceptable carrier or diluent.

19. Method of treating an ailment selected from the group consisting of pain, anxiety, muscular and movement disorders, and an ailment requiring administration of a hypnotic or sedative, comprising the step of administering to a subject in need thereof an effective GABA re-uptake inhibitory amount of a compound of claim 1, alone or in combination with a pharmaceutically-acceptable diluent or carrier, which is effective for alleviation of the said ailment.

20. Method of claim 19 wherein the ailment is epilepsy.

* * * * *

UNITED STATES PATENT AND TRADEMARK OFFICE
CERTIFICATE OF CORRECTION

PATENT NO. : 5,229,404

DATED : July 20, 1993

INVENTOR(S) : Lars J. S. Knutsen, Knud E. Andersen, Anker S. Jørgensen, and Ursula Sonnewald It is certified that error appears in the above-indentified patent and that said Letters Patent is hereby corrected as shown below:

Title page, [73] Assignee; correct spelling of "Bagsvaerd", insert a comma after "Bagsvaerd", and delete "Denmark,".
Col. 1, line 27; insert comma after "(see".
Col. 1, line 36; "In" should be the start of a new paragraph.
Col. 1, formula I; " $A=\text{\textbackslash}O\text{-}(CH_2)_nCH(R^3)(CH_2)_mR^4$ " should read -- $A=N{\diagup}O\text{-}(CH_2)_nCH(R^3)(CH_2)_mR^4$ --.
Col. 2, line 60; "1" should read -- I --.
Col. 3, line 21; insert a comma after "iodo".
Col. 3, line 42; insert a comma after "ethyl".
Col. 3, line 43; insert a comma after "isopropyl".
Col. 4, line 27; "bonyll," should read -- bonyl-1, --.
Col. 4, line 55, formula I; "R" should read -- $R^4$ --.
Col. 4, line 61; "y" should read -- Y --.
Col. 8, line 51; "6 99" should read -- 6.99 --.
Col. 10, line 31; insert a hyphen between "carboxypiperidin" and "1".
Col. 13, line 23; "a nd" should read -- and --.
Col. 13, line 60; insert a comma after "45".
Col. 15, line 60; insert a hyphen between "carboxypiperidin" and "1".
Col. 17, line 42; "(2085" should read -- (20.85 --.
Col. 18, line 32; move the "10" down one line.
Col. 18, line 47; move the "200" down one line.

Col. 19, line 11; insert -- and -- after "pyrrolyl,".
Col. 19, line 18; "trifluoromethy;" should read -- trifluoromethyl; --.
Col. 19, line 22; "II" should read -- III --.
Col. 19, line 34; "NH" should read -- $NH_2$ --.

UNITED STATES PATENT AND TRADEMARK OFFICE
CERTIFICATE OF CORRECTION

PATENT NO. : 5,229,404
DATED : July 20, 1993
INVENTOR(S) : Lars J.S. Knutsen, Knud E. Andersen, Anker S. Jørgensen, and Ursula Sonnewald It is certified that error appears in the above-indentified patent and that said Letters Patent is hereby corrected as shown below:

```
Col. 19, line 35; "of" should read -- a --.
Col. 19, line 36; delete ", and".
Col. 19, line 41; delete "oxazolyl," and "or".
Col. 19, line 48; insert a comma after "hydroxy".
Col. 19, line 58; insert a comma after "claim 1".
```

Signed and Sealed this

Tenth Day of May, 1994

BRUCE LEHMAN

Attest:

Attesting Officer

Commissioner of Patents and Trademarks